United States Patent

Merfeld

(10) Patent No.: US 7,912,542 B2
(45) Date of Patent: Mar. 22, 2011

(54) SENSOR SIGNAL ALIGNMENT

(75) Inventor: Daniel Michael Merfeld, Lincoln, MA (US)

(73) Assignee: Massachusetts Eye & Ear Infirmary, Boston, MA (US)

(*) Notice: Subject to any disclaimer, the term of this patent is extended or adjusted under 35 U.S.C. 154(b) by 219 days.

(21) Appl. No.: 12/272,259

(22) Filed: Nov. 17, 2008

(65) Prior Publication Data

US 2010/0179631 A1    Jul. 15, 2010

Related U.S. Application Data

(63) Continuation of application No. 11/221,477, filed on Sep. 8, 2005, now Pat. No. 7,454,246.

(51) Int. Cl.
*A61N 1/18* (2006.01)
(52) U.S. Cl. .......... 607/2; 607/116; 607/137; 600/9; 600/424; 600/129
(58) Field of Classification Search ............... None
See application file for complete search history.

(56) References Cited

U.S. PATENT DOCUMENTS

| | | | |
|---|---|---|---|
| 6,176,837 B1 * | 1/2001 | Foxlin | 600/595 |
| 6,217,525 B1 * | 4/2001 | Medema et al. | 600/508 |
| 6,409,687 B1 | 6/2002 | Foxlin | |
| 6,546,291 B2 * | 4/2003 | Merfeld et al. | 607/62 |
| 2005/0267549 A1 | 12/2005 | Santina et al. | |
| 2007/0038268 A1 | 2/2007 | Weinberg et al. | |

OTHER PUBLICATIONS

Notification Concerning Transmittal of the International Preliminary Report on Patentability for International Application No. PCT/US2006/033126 dated Mar. 19, 2009.

* cited by examiner

*Primary Examiner* — Carl H. Layno
*Assistant Examiner* — Jon-Eric C. Morales
(74) *Attorney, Agent, or Firm* — Occhiuti Rohlicek & Tsao LLP

(57) ABSTRACT

Methods and systems, including computer readable mediums, are provided for transforming a measurement made relative to a first reference frame into a corresponding measurement relative to a second reference frame. Sensor signals that are produced by sensors in response to the sensors' motion relative to the first reference frame are transformed using a transformation matrix. The transformation generates corrected sensor signals that are relative to the axes of the second reference frame.

20 Claims, 5 Drawing Sheets

SENSOR SIGNAL ALIGNMENT

RELATED APPLICATION

This application is a continuation and claims the benefit of the priority date of U.S. application Ser. No. 11/221,477, filed Sep. 8, 2005, now U.S. Pat. No. 7,454,246, the contents of which are incorporated herein by reference.

GOVERNMENT RIGHTS

This invention was made with support from NIH/NIDCD Grant No. DC 03066 "Adaptation to Controlled Vestibular Stimulation". The United States Government may have certain rights to this invention.

TECHNICAL FIELD

This disclosure relates to transforming a measurement made relative to a first coordinate system into a corresponding measurement that is relative to a desired coordinate system, and more particularly to transforming measurements that are produced by motion sensors of a vestibular prosthesis.

BACKGROUND

The vestibular system is a portion of the inner ear that senses both angular and linear motion of the head, and encodes information representative of that motion as electrical signals. These signals serve as feedback control signals that the brain processes to maintain balance, determine an orientation with respect to surroundings, and cause the body to stand, walk, and perform other functions that require balance and stability.

When the vestibular system becomes damaged, the brain receives fewer feedback control signals, and the feedback control signals that are received may contain incorrect information. A lack of adequate feedback and/or the receipt of incorrect feedback can impair balance and lead to conditions such as vertigo, unsteadiness, dizziness, blurred vision, reduced ability to stand or walk, and cognitive problems. The intensity of these symptoms can range from mild to debilitating. A serious consequence of impaired vestibular function, especially among the elderly, is an increased risk of falling.

Vestibular prostheses have been developed to treat absent or impaired vestibular function by replacing or bypassing damaged vestibular structures in the inner ear. The goal of a vestibular prosthesis is to detect head motion in different directions and, in response to the motion, produce electrical signals that stimulate the vestibular nerve in a way that mimics how the patient's own vestibular system, if functioning properly, would normally stimulate the vestibular nerve.

The anatomy of the vestibular system defines the kind of information that is carried to the vestibular nerve. The vestibular system includes five different organs: two obelisk-shaped organs that sense acceleration and gravity, and three vestibular canals that sense head rotation. The three vestibular canals are nearly orthogonal and define the axes of a head-fixed coordinate system. The vestibular canals provide a measurement of all three dimensions of head rotation as signals that each correspond to rotation about one of the head-fixed axes (i.e., the vestibular canals).

For the signals produced by the vestibular prosthesis to be correctly interpreted by the vestibular nerve, the signals must correspond to rotation about the head-fixed axes, which may be nearly orthogonal. Conventional approaches for appropriately configuring the signals include physically aligning the motion sensors with the vestibular canals during surgery. To obtain a required level of accuracy, these approaches often require painstaking and prolonged surgery. Typically, prolonging the duration of a surgery increases the risk of complication and lengthens the time for recovery.

Other conventional alignment approaches avoid physical alignment of the sensors and instead perform corrections on the sensor signals to make them correspond to rotation about the head-fixed axes before they are delivered to the vestibular nerve. The vestibular prostheses using these approaches generally perform the signal corrections in digital hardware using a variety of digital signal processing (DSP) techniques. For example, such a prosthesis might include an analog-to-digital converter for digitizing each of the motion signals and a microcontroller or digital signal processor for processing the signals via digital floating-point arithmetic. Power consumption associated with digital techniques can be substantial and the speed with which the digital calculations can be performed is limited by clock speed. Increasing the speed of digital processing requires increasing the clock rate, which in turn, requires greater power consumption. Power consumption is an important factor because it determines the life of the prosthesis and the size of the battery that powers the vestibular prosthesis.

SUMMARY

The techniques described herein provide methods and systems, including computer readable mediums, for transforming a measurement made relative to a first reference frame into a corresponding measurement relative to a second reference frame.

In an aspect, the invention features a system that includes a signal measuring system configured to measure sensor signal values produced by sensors in response to the sensors' movement relative to axes of the first reference frame and a computer connected to the signal measuring system. The computer is configured to incorporate the sensor signal values into a sensitivity matrix and calculate an inverse of the sensitivity matrix to obtain a transformation matrix that transforms sensor signals produced by the sensors into corrected signals relative to axes of the second reference frame.

In some embodiments, the system includes correction circuitry that is interfaced to the sensors and configured to store the transformation matrix in memory; receive sensor signals from the sensors; and transform the sensor signals using the transformation matrix to generate corrected sensor signals that are relative to the axes of the second reference frame. For example, the correction circuitry may include analog circuitry and transform the sensor signals in real-time using mathematical operations that are limited to addition operations, subtraction operations, and multiplication operations.

In some embodiments, the sensors and the correction circuitry reside in a vestibular prosthesis. In some embodiments, the sensors are aligned with predefined axes of rotation that are misaligned with the axes of the second reference frame; the signals produced by the sensors correspond to angular motion of the sensors about the predefined axes of rotation; and the corrected signals correspond to signals that the sensors would have produced had the sensors been aligned with the axes of the second reference frame. In other embodiments, the sensors are aligned with predefined axes of linear acceleration that are misaligned with the axes of the second reference frame; the signals produced by the sensors correspond to linear acceleration of the sensors along the predefined axes of linear acceleration; and the corrected signals correspond to signals that the sensors would have produced had the sensors been aligned with the axes of the second reference frame.

In some embodiments, a wireless communication network is provided to transmit the transformation matrix between the computer and the correction circuitry.

In some embodiments, the computer is configured to determine whether the sensitivity matrix is invertible.

In another aspect, the invention features methods and computer readable mediums for transforming a measurement made relative to a first reference frame into a corresponding measurement relative to a second reference frame. The method includes storing a transformation matrix in memory; receiving sensor signals produced by sensors in response to the sensors' motion relative to the first reference frame; and transforming the sensor signals using the transformation matrix to generate corrected sensor signals relative to axes of the second reference frame.

In some embodiments, transforming the sensor signals includes orthogonalizing the sensor signals relative to the axes of a second reference frame. In some embodiments, the sensors are moved with respect to each of the axes of the second reference frame; the signal values that are produced by the sensors in response to the sensors' movement relative to each of the axes of the second reference frame are measured and incorporated into a sensitivity matrix; and an inverse of the sensitivity matrix is calculated to obtain the transformation matrix. The signal values are components of the sensitivity matrix.

In some embodiments, moving the sensors comprises rotating the sensors about each of the axes of the second reference frame. In some embodiments, the corrected sensor signals are sent to a vestibular prosthesis and encoded as stimulation signals. The stimulation signals are then applied to a vestibular nerve. In some embodiments, transforming the sensor signals includes calculating (e.g., in real-time) a product of the transformation matrix and a sensor-signal vector. In some embodiments, calculating an inverse of the sensitivity matrix includes determining that rows of the sensitivity define vectors that are linearly independent; and calculating a transpose of the sensitivity matrix.

Advantages that can be realized from particular implementations of the invention include one or more of the following. The vestibular prosthesis uses a computationally-efficient alignment algorithm to continuously transform sensor signals and deliver them to the vestibular prosthesis and then to the vestibular nerve with minimal delays. The prosthesis can calculate corrected signals at a high-bandwidth and in real-time. The alignment algorithm may be implemented in analog circuitry, digital circuitry, or a combination thereof. The algorithm uses simple mathematical operations that can easily be implemented using low-power analog VLSI (very large scale integration) techniques.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
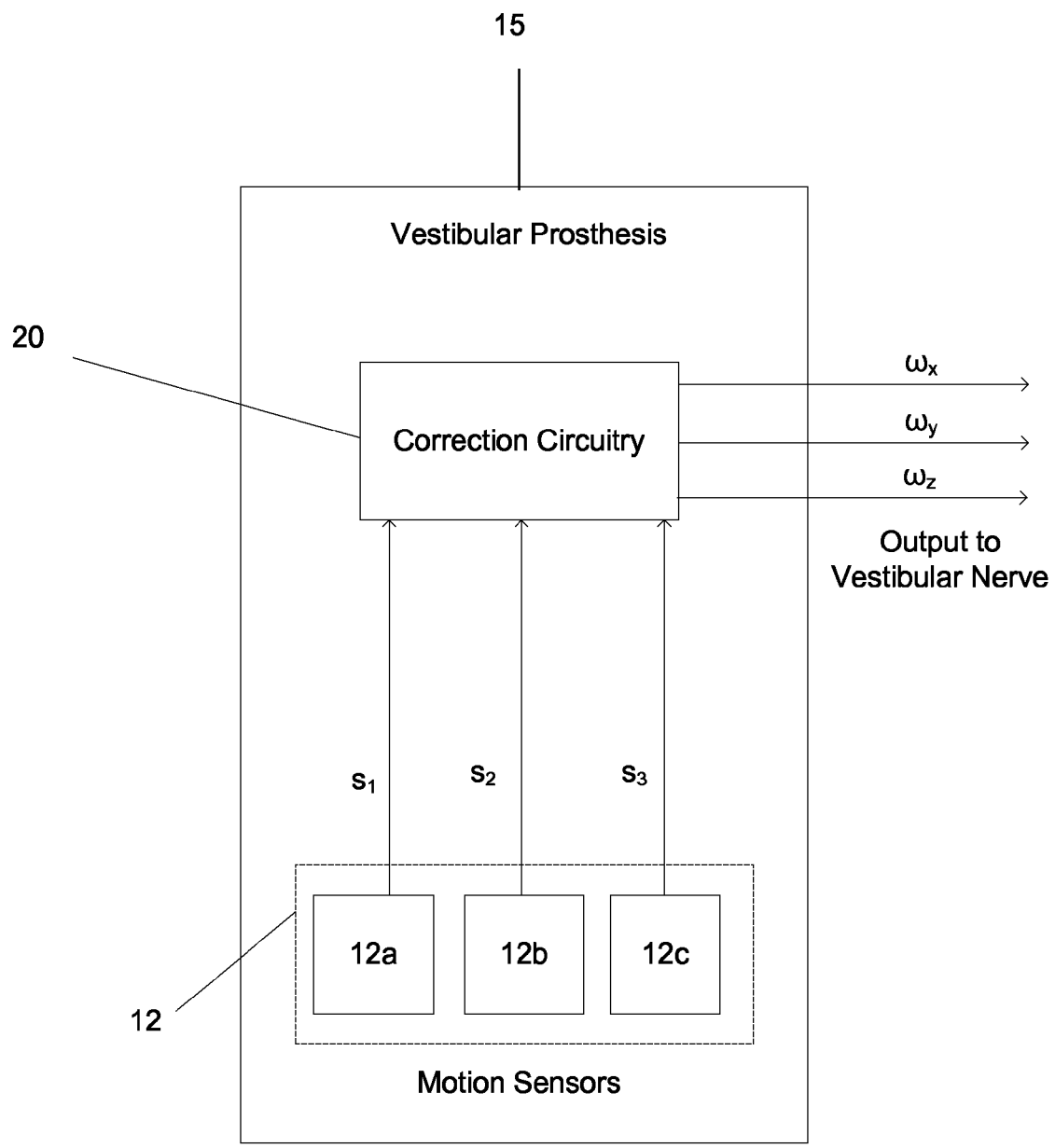
FIG. 1 shows a block diagram of a vestibular prosthesis.

A block diagram of an exemplary vestibular prosthesis 15 is shown in FIG. 1. The vestibular prosthesis 15 includes three motion sensors 12$a$, 12$b$, and 12$c$ (collectively referred to as motion sensors 12) and correction circuitry 20. Similar to a gyroscope, each of the motion sensors 12 has a predefined natural axis of rotation (referred to as a sensitivity axis) and is configured to produce an electric signal in response to being rotated about its sensitivity axis. As seen in FIG. 1, a first motion sensor 12$a$ produces a sensor signal $s_1$, a second motion sensor 12$b$ produces a sensor signal $s_2$, and a third motion sensor 12$c$ produces a sensor signal $s_3$. The sensor signals are one-dimensional values that correspond to the angular motion that the sensors 12 experience along their respective sensitivity axes. The direction of rotation follows the right-hand rule convention. For example, the first sensor signal $s_1$ has a maximum positive value when the first motion sensor 12$a$ rotates counterclockwise directly about its sensitivity axis (i.e., the angle between the first sensor's axis of rotation and the sensitivity axis is zero). Likewise, the first sensor signal $s_1$ has a maximum negative value when the first motion sensor 12$a$ rotates clockwise directly about its sensitivity axis (i.e., the angle between the first sensor's axis of rotation and the sensitivity axis is r radians). If, however, the first motion sensor 12$a$ is rotated along an axis that is perpendicular to the sensor's sensitivity axis, the first sensor signal $s_1$ will be zero.

Figure 3:
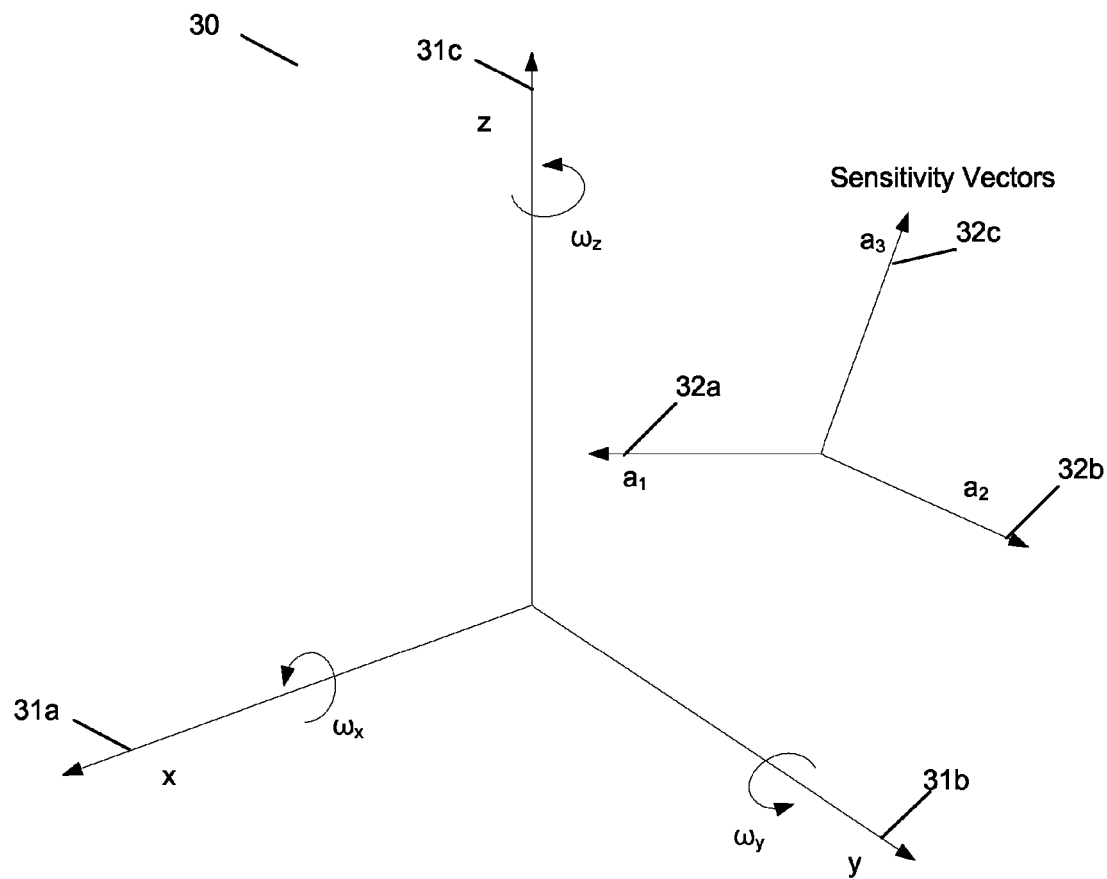
FIG. 3 shows a diagram of sensitivity vectors in a head-fixed coordinate system.

In most cases, when the vestibular prosthesis 15 is implanted into a patient, the sensitivity axes of each of the sensors 12 are misaligned with the head-fixed axes 31$a$-$c$ of the patient's head-fixed coordinate system 30 as shown in FIG. 3. Furthermore, the sensitivity axes may not be orthogonal to each other. However, as long as the sensitivity axes span the space of the head-fixed coordinate system, there exists a transformation matrix, V, that maps the sensor signals onto the axes 31$a$-$c$ of the head-fixed coordinate system 30:

$$Vs = V \begin{bmatrix} s_1 \\ s_2 \\ s_3 \end{bmatrix} = \begin{bmatrix} \omega_x \\ \omega_y \\ \omega_z \end{bmatrix} = \omega, \qquad \text{Eq. 1}$$

where the sensor vector s is a vector whose components are the values of the sensor signals $s_1$, $s_2$, and $s_3$, and the rotation vector $\omega$ is a vector whose components ($\omega_x$, $\omega_y$, $\omega_z$) are the values that correspond to an amount of rotational motion about the head-fixed axes 31$a$-$c$. After the transformation matrix V is obtained, values of the rotational motion ($\omega_x$, $\omega_y$, $\omega_z$) about each of the head-fixed axes (x, y, z) 31$a$-$c$ can be extracted from the sensor signals $s_1$, $s_2$, and $s_3$.

Figure 2:
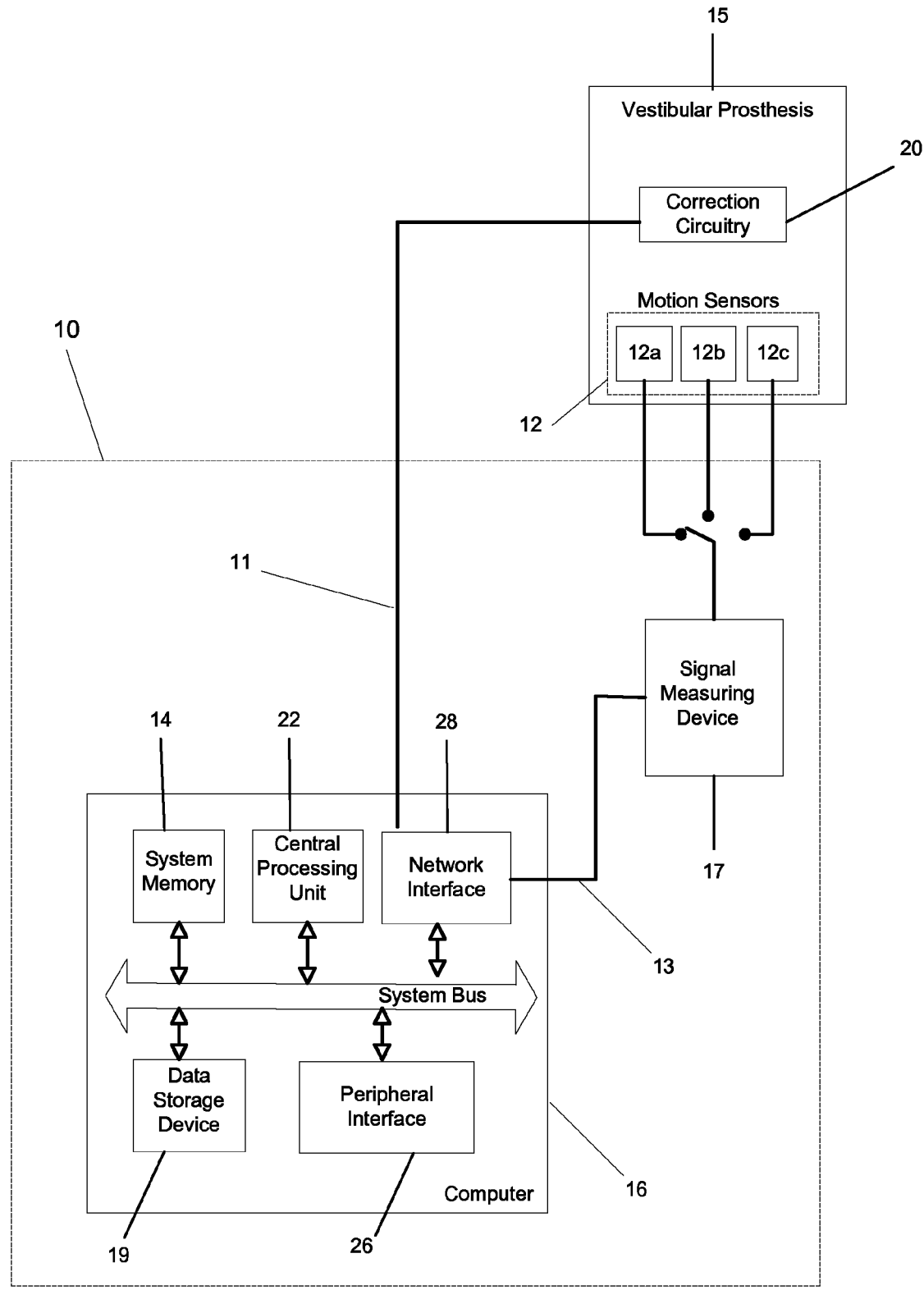
FIG. 2 shows a block diagram of a calibration system for calibrating the motion sensors of the vestibular prosthesis shown in FIG. 1.

Referring to FIG. 2, the correction circuitry 20 transforms the vector s, whose components are the sensor signals $s_1$, $s_2$, and $s_3$, by the transformation matrix V to generate a rotation vector $\omega$ whose components ($\omega_x$, $\omega_y$, $\omega_z$) correspond to the rotational motion about the head-fixed axes 31$a$-$c$. The rotational motion values $\omega_x$, $\omega_y$, and $\omega_z$ correspond to the amount of rotational motion that the sensors 12 would have experienced had their sensitivity axes been both orthogonal to each other and aligned with the head-fixed axes 31a-c. The vestibular prosthesis 15 encodes the rotational motion values $\omega_x$, $\omega_y$, and $\omega_z$ as electrical impulses and then delivers these impulses to the vestibular nerve.

Reducing the complexity and number of operations used by the correction circuitry 20 for transforming the sensor signals $s_1$, $s_2$, and $s_3$ to correspond to rotation motion about the head-fixed axes 31a-c reduces the power consumed by the correction circuitry 20. In some embodiments, the operations performed by the correction circuitry 20 are limited to simple mathematical operations (e.g., addition, multiplication, and subtraction). The correction circuitry 20 may include analog components, digital components, or a combination of both. In some embodiments, the correction circuitry 20 is implemented as an analog VLSI (very-large-scale integration) system. In other embodiments, the correction circuitry 20 may include a digital VLSI system.

The correction circuitry 20 includes memory for storing the transformation matrix V. When the vestibular prosthesis 15 is in use, the correction circuitry 20 transforms the sensor signals $s_1$, $s_2$, and $s_3$ by the transformation matrix V to produce the rotational motion values $\omega_x$, $\omega_y$, and $\omega_z$ that the sensors 12 would have produced had their sensitivity axes been both orthogonal to each other and aligned with the head-fixed axes 31a-c. The transformation matrix V is obtained by measuring the signals produced by each of the motion sensors 12 in response to a rotation about each axis in a head-fixed coordinate system 30. The process 40 for obtaining the transformation matrix V is described below in connection with FIGS. 3 and 4.

FIG. 2 shows an exemplary calibration system 10 for obtaining the transformation matrix V. The calibration system 10 includes a signal measuring system 17 that provides signal measurements indicative of measured values of signals produced by the motion sensors 12 in response to a rotation about each axis in a head-fixed coordinate system 30; a computer 16 for calculating the transformation matrix V from the signal measurements; a first communications bus 13 for sending signal measurement data from the signal measuring system 17 to the computer 16; and a second communications bus 11 for sending the transformation matrix V from the computer 16 to the vestibular prosthesis 15. In exemplary embodiments, the signal measuring system 17 is integrated with the computer 16. Examples of a signal measuring system 17 include, but are not limited to, a voltage meter, a current meter, an analog-to-digital converter, a digital or analog multimeter, an oscilloscope, and a digital analyzer.

The computer 16 includes a data storage device 19, such as a hard drive, for storing data; system memory 14 for storing software; and a central processing unit 22 for executing software stored in the system memory 14. The computer 16 also includes peripheral device interfaces 26 for interfacing peripheral devices such as a mouse, a keyboard, and a monitor; and a communication interface 28 that transmits and receives information over the communication busses 11 and 13.

In exemplary embodiments, either one or both of the communications busses 11 and 13 are replaced by a communications network. Examples of a communications network include a local area network (LAN), a larger group of interconnected systems such as the internet, a private intranet, and other wired and wireless networks.

Figure 4:
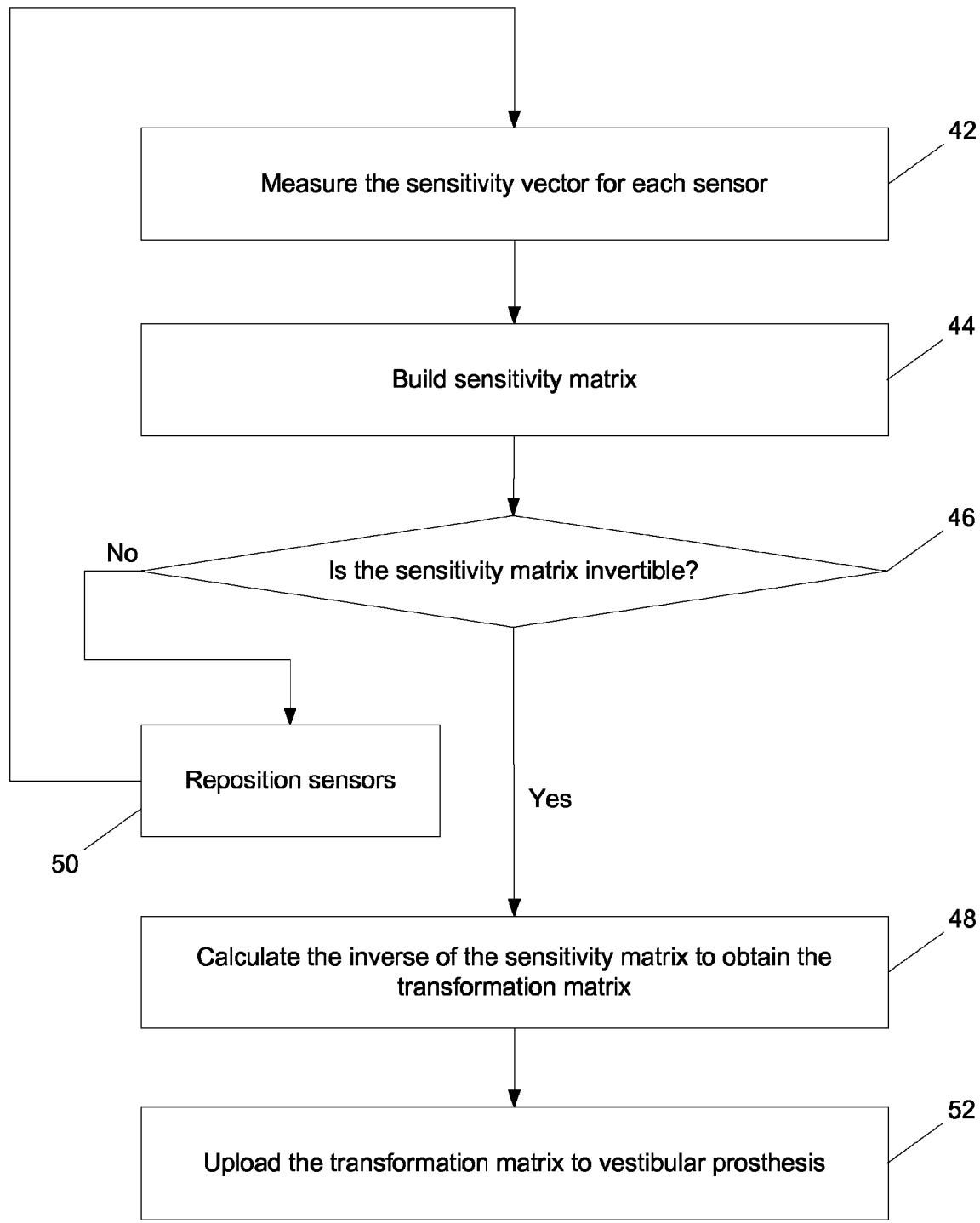
FIG. 4 shows a flowchart of a process performed for determining a transformation matrix that maps signals from the motion sensors to the axes of the head-fixed coordinate system using the calibration system of FIG. 2.

FIGS. 3 and 4 describe a process 40 by which the calibration system 10 of FIG. 2 obtains the transformation matrix V. The three sensors 12 are together rotated about each of the head-fixed axes 31a-c one-by-one. As the sensors 12 rotate about a head-fixed axis (e.g., the x-axis 31a), they produce signal values that correspond to the extent to which they rotate about their respective sensitivity axes. For example, rotating the first sensor 12a about the x-axis 31a of the head-fixed coordinate system 30 yields a value $a_{1x}$ that represents the sensitivity of the first sensor 12a to rotation about the x-axis 31a. Similarly, rotating the first sensor 12a about the y- and z-axes 31b and 31c of the head-fixed coordinate system 30 yields values $a_{1y}$ and $a_{1z}$ that represent the sensitivity of the first sensor 12a to rotation about the y- and z-axes, respectively. From these values, sensitivity vectors 32a-c, denoted $a_1$, $a_2$, and $a_3$, for each of the sensors 12, are determined. The sensitivity vectors 32a-c represent the amplitudes of angular velocity detected about the sensitivity axes of the sensors 12 and the directions of the sensitivity axes with respect to the head-fixed axes 31a-c. For example, the sensitivity vector 32a for the first sensor 12a (denoted $a_1$) can then be expressed as: $a_1 = a_{1x}i + a_{1y}j + a_{1z}k$, where i, j, and k represent unit vectors along the direction of the x-, y-, and z-axes 31a-c of the head-fixed coordinate system 30, respectively.

Similarly, the sensitivity vector 32b of the second sensor 12b is expressed as $a_2 = a_{2x}i + a_{2y}j + a_{2z}k$, where $a_{2x}$, $a_{2y}$, and $a_{2z}$ represent the sensitivity of the second sensor 12b to rotation about the x-, y- and z-axes 31a-c of the head-fixed coordinate system 30; and the sensitivity vector 32c of the third sensor 12c is expressed as $a_3 = a_{3x}i + a_{3y}j + a_{3z}k$, where $a_{3x}$, $a_{3y}$, and $a_{3z}$ represent the sensitivity of the third sensor 12c to rotation about the x-, y- and z-axes 31a-c of the head-fixed coordinate system 30.

The signal measuring system 17 measures the sensitivity vectors 32a-c for each of the motion sensors and stores their values in the data storage device 19 (step 42). In some embodiments, the sensitivity vectors 32a-c are measured after the vestibular prosthesis 15 is implanted in a patient (step 42). In these embodiments, the patient rotates his or her head about each head-fixed axis. In other embodiments, the sensitivity vectors 32a-c are measured before implanting the vestibular prosthesis 15 (step 42). In these embodiments, a machine rotates the vestibular prosthesis 15 about the head-fixed axes 31a-c.

After the sensitivity vectors 32a-c for each of the sensors 12 are measured and stored in the data storage device 19, the central processing unit 22 builds a sensitivity matrix T from the sensitivity vectors 32a-c, where the sensitivity matrix T is expressed as the following:

$$T = \begin{bmatrix} a_1 \\ a_2 \\ a_3 \end{bmatrix} = \begin{bmatrix} a_{1x} & a_{1y} & a_{1z} \\ a_{2x} & a_{2y} & a_{2z} \\ a_{3x} & a_{3y} & a_{3z} \end{bmatrix} \text{(step 44)}. \qquad \text{Eq. 2}$$

In some embodiments, the sensitivity vectors 32a-c are orthonormal. In these embodiments, the sensitivity matrix T is a rotation matrix, R, whose entries (i.e., $a_{ij}$) are equal to the cosines of the angles between the sensitivity vectors 32a-c and the head-fixed axes 31a-c. For example, the entry $a_{1x}$ is equal to the cosine of the angle between the sensitivity vector $a_1$ and the x-axis 31a of the head-fixed coordinate system 30.

The relationship between angular velocity about the head-fixed axes 31a-c and the sensor signals $s_1$, $s_2$, and $s_3$ produced by the sensors 12 is known to be:

$$s = \begin{bmatrix} s_1 \\ s_2 \\ s_3 \end{bmatrix} = T \begin{bmatrix} \omega_x \\ \omega_y \\ \omega_z \end{bmatrix} = T\omega, \qquad \text{Eq. 3}$$

where s is a sensor-signal vector whose components are the values of the sensor signals $s_1$, $s_2$, and $s_3$, T is the sensitivity matrix expressed in Equation 2, and w is a rotation vector whose components ($\omega_x$, $\omega_y$, $\omega_z$) are the values that correspond to rotational motion about each of the head-fixed axes 31a-c. The product $T^{-1}$ T is simply an identity matrix. Therefore, multiplying the sensor-signal vector s by the inverse of the sensitivity matrix $T^{-1}$ yields the rotation vector $\omega$:

$$\omega = \begin{bmatrix} \omega_x \\ \omega_y \\ \omega_z \end{bmatrix} = T^{-1} \begin{bmatrix} s_1 \\ s_2 \\ s_3 \end{bmatrix} = T^{-1} s. \qquad \text{Eq. 4}$$

Comparing Equation 1 to Equation 4, it is apparent that the transformation matrix V is simply the inverse of the sensitivity matrix:

$$V = T^{-1}. \qquad \text{Eq. 5}$$

After the central processing unit 22 builds the sensitivity matrix T, it determines whether or not the sensitivity matrix T is invertible (step 46). The central processing unit 22 may use any appropriate criteria to determine whether the sensitivity matrix is invertible (step 46). For example, the central processing unit 22 may determine if any one of the following statements is true or false.

1. T is row equivalent to a 3×3 identity matrix;
2. T has three pivot positions;
3. The equation Tx=0 has only a trivial solution, x=0;
4. The columns of T are linearly independent; and
5. The determinant of T is non-zero.

If any of the above statements are true, the sensitivity matrix T is invertible, otherwise it is not invertible. In addition to the foregoing invertibility tests, the central processing unit 22 may apply any other invertibility tests for determining whether or not the sensitivity matrix T is invertible. The invertibility tests are stored as software programs in system memory 14.

In most cases, an inverse will exist. However, if two or more of the sensors 12 are positioned such that their sensitivity axes are aligned, the sensitivity matrix T will lack an inverse. In the rare case that central processing unit 22 determines that an inverse is nonexistent, the sensors 12 must be repositioned (step 50). The measuring, building, and determining procedures are then repeated until the central processing unit 22 determines that an inverse exists (steps 42, 44, and 46). In some embodiments, the vestibular prosthesis 15, itself, includes a mechanism for repositioning the sensors 12. In these embodiments, the computer 16 notifies the vestibular prosthesis 15 that no inverse for T exists, and in response, the vestibular prosthesis 15 repositions the sensors 12 (step 50).

If the central processing unit 22 determines that the sensitivity matrix T is invertible, it calculates the inverse of the sensitivity matrix T and stores the inverse in the data storage device 19 (step 48). The inverse of the sensitivity matrix T may be calculated using any appropriate method of matrix inversion. These methods are encoded in software and stored in the system memory 14. Examples of matrix inversion methods include: direct calculation, Gauss-Jordan elimination, Gaussian elimination, LU (lower- and upper-triangle matrix) decomposition, and Moore-Penrose matrix inversion.

In embodiments in which the sensitivity matrix T is simply a rotation matrix R, the inverse ($R^{-1}$) is the same as the transpose ($R^T$) of R. Methods for determining the transpose generally require fewer operations than matrix inversion methods. In some embodiments, the central processing unit 22 determines whether or not the sensitivity matrix T is rotation matrix R before applying a matrix inversion method. Upon determining that the sensitivity matrix T is a rotation matrix R, the central processing unit 22 applies a method for determining its transpose. The computer 16 then uploads the transformation matrix V to the vestibular prosthesis 15 via the first communication bus 11 (step 52).

Figure 5:
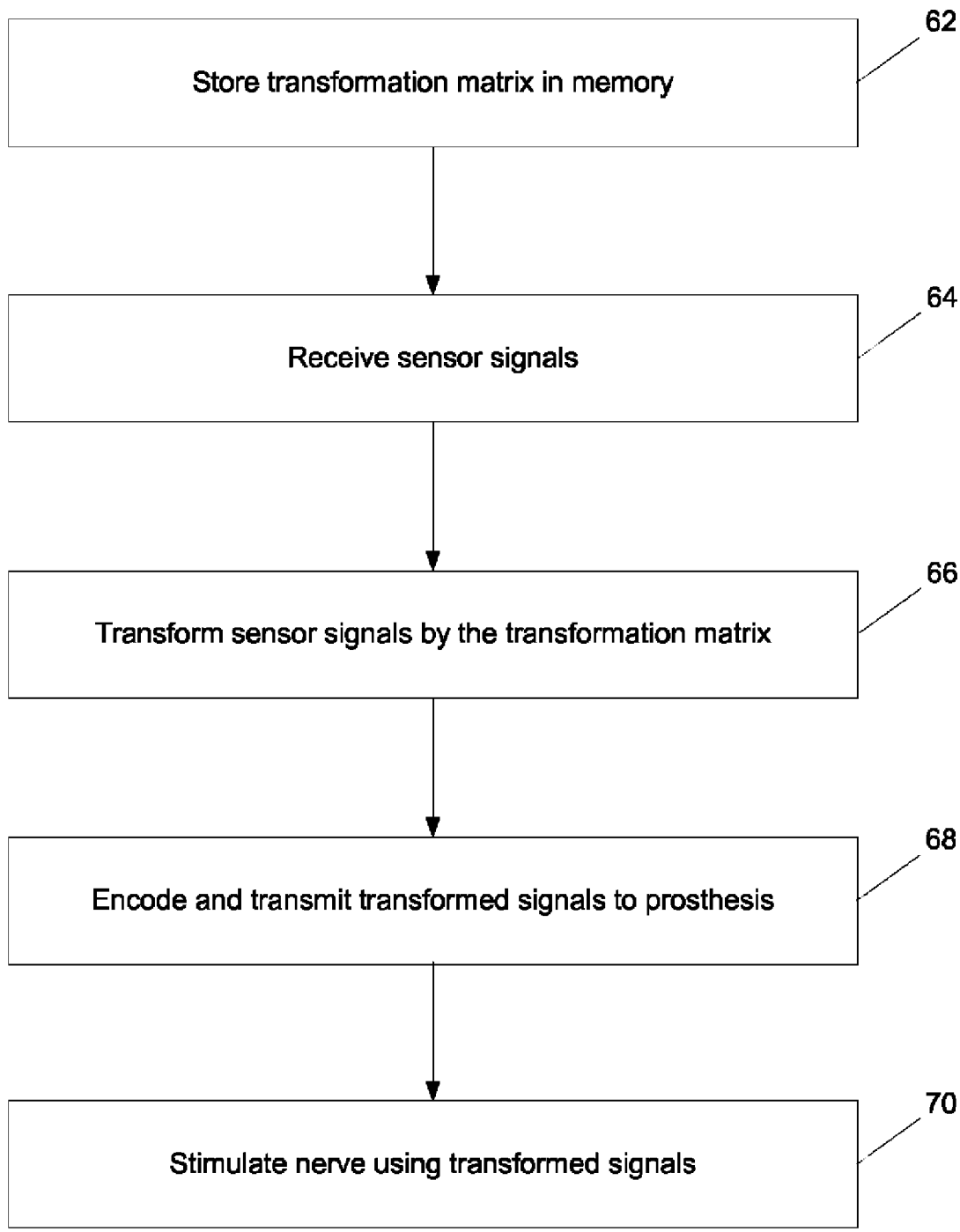
FIG. 5 shows a flowchart of a process by which the vestibular prosthesis of FIG. 1 transforms motion signals relative to the head-fixed coordinate system using the transformation matrix obtained by the process of FIG. 4.

FIG. 5 describes a process 60 by which the transformed motion signals are provided to a vestibular prosthesis 15 so that it can provide the vestibular nerve with appropriate stimulation to encode the rotational motion values $\omega_x$, $\omega_y$, and $\omega_z$ once the signals from the sensors 12 are transformed to the head-fixed axes 31a-c using the transformation matrix V supplied by the computer 16. The process 60 begins with the correction circuitry 20 of the vestibular prosthesis 15 receiving and storing the transformation matrix in memory (step 62). As the motion sensors 12a, 12b, and 12c detect rotational motion of the vestibular prosthesis 15, they generate sensor signals $s_1$, $s_2$, and $s_3$, respectively. The correction circuitry 20 then receives these sensor signals (step 64) and applies the transformation matrix V to the sensor $s_1$, $s_2$, and $s_3$ using Equation 1 to generate the outputs, which are the rotational motion values $\omega_x$, $\omega_y$, and $\omega_z$ (step 66). The calculations include nine multiplications and six additions/subtractions. In some embodiments, the correction circuitry 20 performs the transformation using quaternions, rotation vectors, or related mathematical techniques. This matrix calculation requires only multiplication and addition/subtraction operations. After the correction circuitry 20 calculates the corrected signals $\omega_x$, $\omega_y$, and $\omega_z$, it provides them to the prosthesis (step 68), which then encodes them as a stimulation signal that is transmitted to the vestibular nerve (step 70).

Equation 1 shows the calculations at one instant in time. Since both s and $\omega$ are continuous functions of time, Equation 1 can be expressed as:

$$\begin{bmatrix} \omega_x(t) \\ \omega_y(t) \\ \omega_z(t) \end{bmatrix} = V \begin{bmatrix} s_1(t) \\ s_2(t) \\ s_3(t) \end{bmatrix}, \qquad \text{Eq. 6}$$

where the transformation matrix V is constant, $s_i(t)$ is a sensory signal at a given time t, and $\omega_i(t)$ is a corrected sensory signal at a given time t. The receiving, transforming, and transmitting steps of process 60 are continuously repeated as the motion sensors 12 continually detect motion. In some embodiments, the correction circuitry 20 performs the receiving, transforming, and transmitting steps of process 60 in real time.

The calibration system 10 and the vestibular prosthesis 15, including the correction circuitry 20, are not limited to the hardware and software described above and may contain components and extensions that are different from those described above. The calibration system 10 and the vestibular prosthesis 15 can be implemented in digital electronic circuitry, or in computer hardware, firmware, software, or in combinations thereof.

The functions of the calibration system 10 and vestibular prosthesis 15 can be implemented, at least in part, via a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one machine or on multiple machines at one site or distributed across multiple sites and interconnected by a communication network.

Method steps associated with the calibration system 10 and the vestibular prosthesis 15 can be performed by one or more programmable processors executing one or more computer programs to perform the functions of the processes. All or part of the calibration system 10 and the vestibular prosthesis 15 can be implemented as special purpose logic circuitry, e.g., an FPGA (field programmable gate array) and/or an ASIC (application-specific integrated circuit). All or part of the calibration system 10 and the vestibular prosthesis 15 can be implemented as analog circuitry, e.g., analog VLSI circuitry.

Processors suitable for the execution of a computer program include, by way of example, both general and special purpose microprocessors, and any one or more processors of any kind of digital computer. Generally, a processor will receive instructions and data from a read-only memory or a random access memory or both. Elements of a computer include a processor for executing instructions and one or more memory devices for storing instructions and data.

The circuitry described herein, including the central processing unit 22, signal measuring device 17, correction circuitry 20, and motion sensors 12, may be implemented as part of the calibration system 10 and the vestibular prosthesis 15, or as separate circuitry for use in conjunction with the calibration system 10 and the vestibular prosthesis 15. Furthermore, the vestibular prosthesis 15 may be configured to include all or any combination of components of the calibration system 10.

The signal processing techniques described above in relation to the processes 40 and 60 for rotational sensors (angular accelerometers or angular rate sensors) are also applicable to translational motion sensors (e.g., linear accelerometers) and are, in fact, generally applicable to any system that requires that two or more vector signals be orthogonal to one another. Examples of vector signals are angular velocity, angular acceleration, linear velocity, linear acceleration, force, displacement, electric fields, magnetic fields, etc. Since the process of transformation described herein is generally applicable, the techniques also apply to any system in which signals (including signals that are not motion based) require a coordinate transformation and for which a transformation matrix can be calculated. The techniques are applicable to any system that requires a coordinate rotation, orthogonalization, or transformation. Furthermore the techniques are generally applicable to any system that requires both rotation and orthogonalization transformations.

A number of embodiments of the invention have been described. Nevertheless, it will be understood that various modifications may be made without departing from the spirit and scope of the invention. Accordingly, other embodiments are within the scope of the following claims.

What is claimed is:

1. A computer implemented method for transforming a measurement made relative to a first reference frame into a corresponding measurement relative to a second reference frame, the method comprising causing a computer to execute instructions to:
   store a transformation matrix in memory;
   receive sensor signals produced by vestibular motion sensors in response to the sensors' motion relative to the first reference frame; and
   transform the sensor signals using the transformation matrix to generate corrected sensor signals relative to axes of the second reference frame wherein to transform the sensor signals includes orthogonalizing the sensor signals to align with orthogonal axes of the second reference frame.

2. The method of claim 1, further comprising:
   moving the sensors with respect to each of the axes of the second reference frame;
   measuring signal values produced by the sensors in response to the sensors' movement relative to each of the axes of the second reference frame;
   incorporating the signal values into a data structure representing a sensitivity matrix, wherein the signal values are components of the sensitivity matrix; and
   calculating an inverse of the sensitivity matrix to obtain the transformation matrix.

3. The method of claim 2, wherein moving the sensors comprises rotating the sensors about each of the axes of the second reference frame.

4. The method of claim 2, wherein calculating an inverse of the sensitivity matrix comprises:
   determining that rows of the sensitivity matrix define vectors that are linearly independent; and
   calculating a transpose of the sensitivity matrix.

5. The method of claim 1, wherein to transform the sensor signals comprises calculating the corrected sensor signals in real-time.

6. The method of claim 1, wherein to transform the sensor signals comprises calculating a product of the transformation matrix and a sensor-signal vector that includes, as elements, the sensor signal from each sensor.

7. The method of claim 1, further comprising receiving an analog signal to be used for generating corrected sensor signals.

8. A system for transforming a measurement made relative to a first reference frame into a corresponding measurement relative to a second reference frame, the system comprising:
   a signal measuring system configured to measure sensor signal values produced by vestibular motion sensors in response to the sensors' movement relative to axes of the first reference frame;
   a computer connected to the signal measuring system, wherein the computer is configured to:
   incorporate the sensor signal values into a sensitivity matrix; and
   calculate an inverse of the sensitivity matrix to obtain a transformation matrix that transforms sensor signals produced by the vestibular motion sensors into corrected signals relative to axes of the second reference frame.

9. The system of claim 8, further comprising:
   correction circuitry interfaced to the sensors, the correction circuitry configured to:
   store the transformation matrix in memory;
   receive sensor signals from the sensors; and transform the sensor signals using the transformation matrix to generate corrected sensor signals that are relative to the second reference frame.

10. The system of claim 9, wherein:
the sensors are aligned with predefined axes of rotation that are misaligned with the axes of the second reference frame;
the signals produced by the sensors correspond to angular motion of the sensors about the predefined axes of rotation; and
the corrected signals correspond to signals that the sensors would have produced had the sensors been aligned with the axes of the second reference frame.

11. The system of claim 9, wherein:
the sensors are aligned with predefined axes of linear acceleration that are misaligned with the axes of the second reference frame;
the signals produced by the sensors correspond to linear acceleration of the sensors along the predefined axes of linear acceleration; and
the corrected signals correspond to signals that the sensors would have produced had the sensors been aligned with the axes of the second reference frame.

12. The system of claim 9, wherein the correction circuitry is further configured to transform the sensor signals in real-time.

13. The system of claim 9, wherein the correction circuitry comprises analog circuitry.

14. The system of claim 9, wherein the correction circuitry is further configured to transform the sensor signals using mathematical operations that are limited to addition operations, subtraction operations, and multiplication operations.

15. The system of claim 9, further comprising a wireless communication network configured to transmit the transformation matrix between the computer and the correction circuitry.

16. The system of claim 8, wherein the computer is configured to determine whether the sensitivity matrix is invertible.

17. A non-transitory computer readable medium having, stored thereon, software for transforming a measurement made relative to a first reference frame into a corresponding measurement relative to a second reference frame, the software comprising instructions for causing a computer to:
store a transformation matrix in memory;
receive sensor signals produced by vestibular motion sensors in response to the sensors' motion relative to the first reference frame; and
transform the sensor signals using the transformation matrix to generate corrected sensor signals that correspond to the signals that the vestibular motion sensors would have produced had the vestibular motion sensors been aligned with the axes of the second reference frame, wherein the instructions for causing the computer to transform the sensor signals include instructions for orthogonalizing the sensor signals to align with orthogonal axes of the second reference frame.

18. The computer readable medium of claim 17, wherein the software further comprises instructions that cause the computer to:
move the sensors with respect to each of the axes of the second reference frame;
measure signal values produced by the sensors in response to the sensors' movement relative to each of the axes of the second reference frame;
incorporate the signal values into a data structure representing a sensitivity matrix, wherein the signal values are components of the sensitivity matrix; and
calculate an inverse of the sensitivity matrix to obtain the transformation matrix.

19. The computer readable medium of claim 17, wherein the software further comprises instructions that cause the computer to rotate the sensors about each of the axes of the second reference frame.

20. The computer readable medium of claim 17, wherein the software further comprises instructions that cause the computer to:
determine that rows of the sensitivity matrix define vectors that are linearly independent;
calculate a transpose of the sensitivity matrix;
calculate a product of the transformation matrix and a sensor-signal vector that includes, as elements, the sensor signal from each sensor; and
calculate the corrected signals in real-time.

* * * * *

UNITED STATES PATENT AND TRADEMARK OFFICE
CERTIFICATE OF CORRECTION

PATENT NO. : 7,912,542 B2  
APPLICATION NO. : 12/272259  
DATED : March 22, 2011  
INVENTOR(S) : Daniel Michael Merfeld Page 1 of 1

It is certified that error appears in the above-identified patent and that said Letters Patent is hereby corrected as shown below:

In the Specification

Column 1, Lines 12-15, delete "support from NIH/NIDCD Grant No. DC 03066 Adaptation to Controlled Vestibular Stimulation. The United States Government may have certain rights to this invention." and insert -- government support under Grant Number DC003066 awarded by the National Institutes of Health. The government has certain rights in the invention. --

Signed and Sealed this  
Thirteenth Day of April, 2021

Drew Hirshfeld  
*Performing the Functions and Duties of the*  
*Under Secretary of Commerce for Intellectual Property and*  
*Director of the United States Patent and Trademark Office*